United States Patent [19]
Creighton

[11] 3,941,790
[45] Mar. 2, 1976

[54] BIS DIKETOPIPERAZINES
[75] Inventor: Andrew Malcolm Creighton, London, England
[73] Assignee: National Research Development Corporation, England
[22] Filed: Feb. 21, 1974
[21] Appl. No.: 444,485

Related U.S. Application Data
[60] Division of Ser. No. 310,700, Nov. 30, 1972, abandoned, which is a continuation-in-part of Ser. No. 126,276, March 19, 1971, abandoned, which is a continuation-in-part of Ser. No. 741,874, July 2, 1968, abandoned.

[30] Foreign Application Priority Data
July 3, 1967   United Kingdom............... 30617/67

[52] U.S. Cl. 260/268 DK; 260/268 BF; 260/561 R; 260/583 R; 424/250
[51] Int. Cl.² ..................................... C07D 295/10
[58] Field of Search ................. 260/268 BI, 268 DK

[56] References Cited
UNITED STATES PATENTS
2,628,963   2/1953   Laucius et al. ..................... 260/376
3,196,153   7/1965   Dazzi ............................. 260/268 BI FOREIGN PATENTS OR APPLICATIONS
978,724   12/1964   United Kingdom............ 260/268 BI OTHER PUBLICATIONS
K. Hellmann et al., *Nature*, 1969, 224, 273.

Hellmann et al., *Brit. Med. Jour.*, 1969, i, 822.
Creighton et al., *Nature*, 1969, 222, 384.
Badinand, "Bull, Soc. Chim. France," 1960, pp. 382–383.
Morrison et al., "Organic Chemistry" 1966, pp. 76–84.

*Primary Examiner*—Donald G. Daus
*Assistant Examiner*—David E. Wheeler

[57]   ABSTRACT

A pharmaceutical composition useful for aiding regression and palliation of cancer in mammals comprises a therapeutically effective amount of a compound of formula

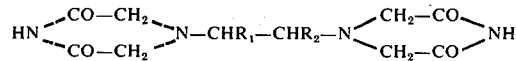

wherein $R_1$ and $R_2$ are each separately selected from hydrogen and methyl or together represent an ethylene bridging group, with the proviso that when both of the groups $R_1$ and $R_2$ are methyl they are disposed in the meso configuration, or a non-toxic salt thereof with a physiologically acceptable inorganic or organic acid, in combination with a physiologically acceptable diluent or carrier.

7 Claims, No Drawings

BIS DIKETOPIPERAZINES

The present application is a divisional application derived from my application Ser. No. 310,700, filed Nov. 30, 1972 now abandoned, which is a continuation-in-part of Ser. No. 126,276, filed Mar. 19, 1971, now abandoned, which is in turn a continuation-in-part derived from my application Ser. No. 741,874, filed July 2, 1968 and now abandoned.

This invention relates to pharmaceutical compounds, to processes for their preparation and to compositions containing them, and is primarily concerned with substances having activity in relation to certain forms of cancer, including leukemia, and certain non-malignant forms of proliferative disease.

It has been discovered that certain chemical compounds, some of which are already known and have been described as possessing properties unconnected with biological chemistry, display a significant degree of activity against tumours and other forms of cancer, and against certain non-malignant forms of proliferative disease, whilst being of relatively low toxicity. These compounds are characterised by a chemical structure which does not appear to have been previously explored in biological research and which is the bis(3,5-dioxopiperazin-1-yl) alkane structure of formula (I):

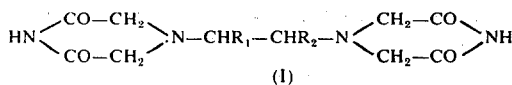

wherein $R_1$ and $R_2$ are each separately selected from hydrogen and methyl or together constitute an ethylene bridging group, provided that where the groups $R_1$ and $R_2$ are both methyl they are in a meso stereochemical relationship.

The present invention comprises compounds of the above formula and salts thereof with physiologically acceptable inorganic and organic acids, and their use in compositions intended for mammalian administration and containing or associated with a physiologically acceptable diluent or carrier.

Compounds having the structure defined above include or are related to certain of the poly-N-diacetic acid imides specifically described in U.K. patent specification No. 978,724 in which an extensive class of compounds is proposed as levelling agents, intermediates, textile auxiliaries, and curing agents. It must be emphasized, however, that the possession of anti-cancer properties is by no means co-extensive with the possession of the non-biological utilities mentioned, and the great majority of compounds embraced by the prior specification are totally devoid of the biological properties under consideration. Indeed, the degree of specificity of anti-cancer activity is such that whilst meso-2,3-bis(3,5-dioxopiperazin-1-yl)butane (I,$R_1$ = $R_2$ = $CH_3$) has been found to show significant activity in this respect, its racemic analogue, dl-2,3-bis(3,5-dioxopiperazin-1-yl)butane, is essentially inactive. It is also to be noted that the anti-malignant activity exhibited by the compounds defined herein contrasts with the lack of activity in ethylene diamine tetra-acetic acid itself and simple derivatives thereof such as the lower alkyl esters.

Of the compounds according to the present invention, 1,2-bis(3,5-dioxopiperazin-1-yl) propane (I,$R_1$ = H, $R_2$ = $CH_3$) is of particular interest, whether in the dl, d or l form.

Several methods are available for the preparation of the compounds of formula (I). Thus for example, they can be prepared by reaction of the corresponding tetra-acetic acid of formula (II) with formamide, the reaction usually being carried out in excess of formamide as the solvent and at an elevated temperature, preferably under nitrogen.

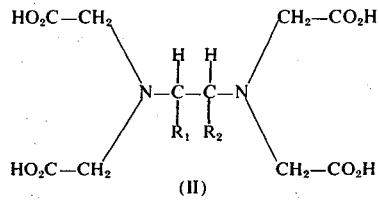

Alternatively, and with particular advantage when the tetra-acetic acid (II) has a tendency to decarboxylate on heating, the compounds may be prepared by heating the corresponding tetra-amide in polyphosphoric acid or phenol.

A further alternative also exists, having the advantage of being a lower temperature method, which comprises treating the corresponding tetranitrile with sodamide in formamide and treating the resulting product with hydrogen chloride in methanol. It will be appreciated that the tetra-acetic acid, tetra-amide or tetranitrile employed should, where appropriate, be of the correct stereochemical relationship.

The tetra-acetic acids of formula (II) may be obtained from the corresponding succinic acid of formula (III), which again should be of the correct stereochemical relationship.

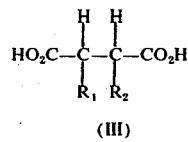

The compounds of the present invention are of value in the treatment of a wide variety of forms of cancer including carcinomas, sarcomas including lymphosarcomas, leukemias and Hodgkin's disease, and 1,2-bis(3,5-dioxopiperazin-1-yl)propane, in particular, has the added advantage that it shows a marked degree of inhibition of metastases. Experimental cancers against which the compounds have proved effective include sarcoma 180, adenocarcinoma 755, the Walker 256, Yoshida and Lewis lung tumours, the Cloudman melanoma, and the leukemia L1210, and clinical trials in patients with a variety of forms of cancer have been carried out and are referred to hereinafter. It is of some interest that dl-1,2-bis(3,5-dioxopiperazin-1-yl)propane has been found to be effective against inter-cerebrally implanted leukemia L1210, since this is indicative of the ability of the compound to cross the blood-brain barrier. The utility of the compounds is, however, not restricted to the treatment of cancer and they also find application in the treatment of certain non-malignant forms of proliferative disease and particularly psoriasis. It will be appreciated that individual compounds within the scope of the invention may show differing spectra of pharmaceutical activity and that a particular compound or compounds may be of especial value for the treatment of any particular form of cancer. Furthermore, the utility of the compounds of the present invention in aiding regression and palliation of cancer in mammals extends to their use in conjunction with other forms of treatment for this disease. Thus, for example, these compounds may be combined with other compounds having anti-cancer properties, such as methotrexate, and in some instances a synergistic effect is observed.

The compounds may be formulated for use as pharmaceuticals by a variety of methods. For instance, they may be applied as aqueous, oily (e.g., as a suspension in isopropyl myristate), or in some cases emulsified compositions for parenteral administration and therefore preferably sterile and pyrogen-free. In general, they have rather low solubility in aqueous media and are therefore usually administered in the form of aqueous suspensions containing suitable surface active agents. Without commitment to a rigid definition of dosages it may be stated that the normal daily dosage of active constituent which is proposed for mammalian use lies in the range from about 10 milligrams to about 3 grams, but preferably from about 25 milligrams to about 3 grams. It will be appreciated that these daily dosages may be divided into two or more portions, for example three or even five, and, indeed, the administration during the day of several smaller doses may prove advantageous as compared with a single larger dose. Furthermore the daily dosage will vary somewhat according to the particular compound used and its mode of administration. Thus doses as indicated above may be given as a solution in about 500–1000 mls. of liquid for intravenous injection by slow infusion, or as a solution or suspension in about 10 ml. by the intramuscular route, or in small volumes subcutaneously. In some instances, however, and particularly in the case of oral administration, the daily dosage may be selected in a range with a higher minimum and maximum, for example from 250 or 500 milligrams up to 1 to 3 or on occasion even as high as 10 grams. For oral administration conventional carrier materials such as starch, lactose, dextrin, and magnesium stearate may be used, whilst for the treatment of local forms of the disease, suitable creams or drops may be prepared. Other types of formulation include aerosols, cachets, suppositories, etc.

When the compounds are to be formulated as salts, preferred formulations are prepared with methane sulphonic acid, isethionic acid, tartaric acid and other solubilizing acids. Salts thus formed are frequently difficult to isolate in view of the weak basicity of some of the parent compounds but their aqueous solutions, after adjustment to physiologically acceptable pH with buffers, are stable for extended periods of time. Solutions of similar strength, i.e., 0.5% (w/v), are also obtainable with hydrochloric acid.

Although the invention is restricted to one stereoisomeric form as far as certain compounds are concerned, others can exist in different stereoisomeric forms, thus the cyclo-butane analogue $(I, R_1R_2 = C_2H_4)$ can exist in a trans form and also a cis form. The d and l forms of the propane analogue individually, when each is obtained substantially free from the other and from the dl form, shown no substantial difference in biological activity from that observed for the racemic dl mixture. The individual stereoisomers do, however, possess an advantage over the mixture in that their individual aqueous solubilities, which are substantially similar, are appreciably greater than the aqueous solubility of the mixture. Thus, for example, a saturated solution of l-1,2-bis(3,5-dioxopiperazin-1-yl)propane in water at room temperature contains about 1.1% (w/v) of the compound whereas a similar solution of the dl form contains only about 0.1% (w/v). This means, for example, that the neutral compound can be administered parenterally in a much smaller volume if given in the form of either of the individual stereoisomers.

The invention is illustrated by the following Examples:

EXAMPLE 1

1,2-bis(3,5-Dioxopiperazin-1-yl)ethane 1,2-Diaminoethane tetra-acetic acid (900 g.) and formamide (2.5 liters) are heated together under reduced pressure (ca 100 mm.) at 110°–120°C for 75 minutes. The temperature is then raised to 155°–160°C and heating continued for a total of 5 hours (complete solution is obtained after ca 35 minutes at 155°–160°C and the product begins to precipitate out about 20–30 minutes later when frothing may become a temporary problem). The reaction mixture is allowed to cool to room temperature and then stood in the refrigerator overnight. Filtration, followed by washing consecutively with cold formamide, ethanol and petroleum ether (b.p. 60°–80°C), and drying in vacuo at 60°C, gives 1,2-bis(3,5-dioxopiperazin-1-yl)ethane (664 g. 85%) as colorless needles, m.p. 297°–300°C (dec.).

EXAMPLE 2 dl-1,2-bis(3,5-Dioxopiperazin-1-yl)propane 1,2-Diaminopropane tetra-acetic acid (100 g.) and formamide (400 ml.) are heated together at reduced pressure under nitrogen at 100°–110°C for 1 hour, and then at 150°–155°C for 4 hours. The brown solution is evaporated under reduced pressure at 80°–90°C and the residue taken up in methanol (120 ml.) and cooled in the refrigerator overnight. Filtration, followed by washing with cold methanol and vacuum drying at 65°C gives dl-1,2-bis(3,5-dioxopiperazin-1-yl)propane (62 g. 70%) as a very pale cream microcrystalline solid, m.p. 237°–239°C.

EXAMPLE 3 d-1,2-bis(3,5-Dioxopiperazin-1-yl)propane d-1,2-Diaminopropane tetra-acetic acid monohydrate, $[\alpha]_D + 47.1°$ (c. 0.5% in water), prepared essentially by the method of Dwyer and Garvan, *J. Amer. Chem. Soc.*, 1959, 81, 2956, is reacted with formamide by the method described in Example 2 to give a 43% yield of d-1,2-bis(3,5-dioxopiperazin-1-yl)propane, $[\alpha]_D + 11.35°$ (c. 5% in dimethyl-formamide), m.p. 193°C after recrystallisation from aqueous methanol/ether.

EXAMPLE 4 l-1,2-bis(3,5-Dioxopiperazin-1-yl)propane l,1,2-Diaminopropane tetra-acetic acid monohydrate, $[\alpha]_D - 44.2°$ (c. 0.5% in water), prepared essentially by the method of Dwyer and Garvan (loc. cit.), is reacted with formamide by the method described in Example 2 to give a 36% yield of l-1,2-bis(3,5-dioxopiperazin-1-yl)propane, $[\alpha]_D - 10.9°$ (c. 5% in dimethyl-formamide), m.p. 193°–194°C after recrystallization from aqueous methanol/ether.

EXAMPLE 5 meso-2,3-bis(3,5-Dioxopiperazin-1-yl)butane meso-2,3-Diaminobutane [m.p. of dihydrochloride 325°C (dec.); m.p. of diacetyl derivative, 300°–301°C] is prepared by lithium aluminum hydride reduction in ether during 4 days of the dibenzyl ether of dimethyl glyoxime and isolated as the dihydrochloride. The dihydrochloride is converted in 32% yield, essentially by the method described by Dwyer and Garvan (loc. cit.) for the 1,2-diaminopropane derivative but using an extra two equivalents of base, to meso-2,3-diaminobutane tetra-acetic acid dihydrate, m.p. 149°C (dec.).

meso-2,3-Diaminobutane tetra-acetic acid dihydrate is reacted with formamide, essentially by the method described in Example 2 but diluting the final reaction mixture with acetone rather than concentrating it, to give a 34% yield of meso-2,3-bis(3,5-dioxopiperazin-1-yl)butane, m.p. 320°C (dec.).

EXAMPLE 6 trans-1,2-bis(3,5-Dioxopiperazin-1-yl)cyclobutane trans-1,2-Diaminocyclobutane tetra-acetic acid monohydrate, m.p. 234°–235°C (dec.), prepared in 56% yield essentially by the method of Dwyer and Garvan (loc. cit.), is reacted with formamide according to the procedure followed in Example 2 to give a 69% yield of trans-1,2-bis(3,5-dioxopiperazin-1-yl)cyclobutane, m.p. 257°–259°C (dec.).

EXAMPLE 7

1,2-bis(Dioxopiperazin-1-yl)ethane

N,N,N',N'-Tetracarboxamidomethyl-1,2-diaminoethane (0.5 g. prepared by the method of Badinard et al., *Bull Soc. Chim. France*, 1960, 382), is added to polyphosphoric acid [prepared by heating phosphorus pentoxide (5 g.) and orthophosphoric acid (5 ml.) at 120°C for 2 hours and allowing to cool to 25°C] and the mixture is heated at 105°C for 10 minutes and then at 120°C for a further 30 minutes. The viscous brown solution is cooled, treated with ice and neutralized by the addition of 0.880 aqueous ammonia (ca 10 ml.) when 1,2-bis(3,5-dioxopiperazin-1-yl)ethane (0.33 g. 65%) is precipitated as a very pale pink microcrystalline solid, m.p. 298°–300°C.

EXAMPLE 8 dl-1,2-bis(3,5-Dioxopiperazin-1-yl)propane

N,N,N',N'-Tetracarboxamidomethyl-1,2-diaminopropane (0.5 g.), prepared essentially by the method of Badinard et al. (loc. cit.), and phenol (10 g.) are heated together under nitrogen at 165°C for 20 hours. The phenol is removed by evaporation under reduced pressure and the residue triturated with methanol, cooled in ice and filtered to give dl-1,2-bis(3,5-dioxopiperazin-1-yl) propane (0.44 g., 82%) m.p. 235°–236°C.

EXAMPLE 9

1,2-bis(3,5-Dioxopiperazin-1-yl)ethane

The procedure of Example 8 is followed using N,N,N',N'-tetracarboxamidomethyl-1,2-diaminoethane and gives rise to a 85% yield of the same product as obtained in Example 1.

EXAMPLE 10

Formulation i. Tablets of the following composition are prepared:

|  | mg./tablet |
|---|---|
| The product of Example 1 (micronized) | 250 |
| "Avicel" (microcrystalline cellulose) | 38 |
| polyvinylpyrrolidone | 3 |
| alginic acid | 6 |
| magnesium stearate | 3 |

The product of Example 1 is mixed with the "Avicel" and polyvinyl pyrrolidone is added dissolved in sufficient industrial methylated spirits 74°OP to produce a mass suitable for granulating. The mass is granulated through a 20 mesh sieve (the British mesh standard is used throughout the specification) and the resultant granules are dried at a temperature not exceeding 50°C. The dried granules are passed through a 20 mesh sieve and the alginic acid and magnesium stearate are then added and mixed with the granules. The product is compressed into tablets, each weighing 300 mg., on ⅜ in. flat bevelled edge divider punches.

ii. Tablets of the following composition are prepared:

|  | mg./tablet |
|---|---|
| The product of Example 2 | 250 |
| "Avicel" (microcrystalline cellulose) | 134 |
| polyvinylpyrrolidone | 4 |
| alginic acid | 8 |
| magnesium stearate | 4 |

The tablets are prepared by essentially the same procedure as described in Example 10, and are compressed at a tablet weight of 400 mg. on 7/16 in. flat bevelled edge punches.

iii. Tablets of the following composition are prepared:

|  | mg./tablet |
|---|---|
| The product of Example 1 (micronized) | 250 |
| lactose (300 mesh) | 19 |
| maize starch | 15 |
| gelatine | 10 |
| magnesium stearate | 6 |

The tablets are prepared by mixing the product of Example 1 with lactose and half the total quantity of maize starch required, and adding to the mass a 5% (w/v) solution of gelatine in water. The product is granulated through a 16 mesh sieve, and the resultant granules are dried to constant weight at a temperature not exceeding 60°C. The dried granules are passed through a 20 mesh sieve and mixed with magnesium stearate and the remainder of the maize starch. The product is compressed at 300 mg. tablet weight on ⅜ in. flat bevelled edge divided punches.

iv. The product of Example 2 (0.548 g.) is added to 5 ml. of a 0.4N solution of (1) hydrochloric acid, (2) isethionic acid, (3) methane sulphonic acid, or (4) tartaric acid, and the mixture is made up to 100 ml. by the addition of water. The solution so obtained is added to an aqueous solution of disodium hydrogen phosphate (0.2M, 10 ml.) to provide a stable solution having a pH of 5.7. Injection of the solution within 1 hour of preparation is recommended.

EXAMPLE 11

Laboratory Tests

The overall effects of various compounds on the rate of synthesis of DNA is mammalian cell cultures are determined with the method of Birnie and Simons (Experimental Cell Research, 1967, 46, 355) by measuring the changes in the amount of $^3$H-thymidine incorporated in 1 hour by secondary mouse fibroblast cultures which have been incubated with a particular compound for 22 hours.

Typical results illustrating the degree of inhibition of $^3$H-thymidine incorporation for the treated fibroblasts as compared with untreated fibroblasts are given in Table I. The results obtained can be regarded as a measure of cytotoxicity and correlate well with results obtained with implanted tumors in mice.

TABLE I

| Structure | Concentration of compound μg./ml. | %Inhibition |
|---|---|---|
| HN–N–CH$_2$–CH$_2$–N–NH (bis-dioxopiperazinyl) | 8<br>0.3 | 69<br>21 |
| >N–CH(CH$_3$)–CH$_2$–N<  dl | 5<br>1<br>0.3 | 63<br>48<br>15 |
| >N–CH(CH$_3$)–CH$_2$–N<  d | 200<br>1 | 74<br>44 |
| >N–CH(CH$_3$)–CH$_2$–N<  l | 200<br>1 | 72<br>52 |
| >N–CH–CH–N<  trans (–CH$_2$–CH$_2$–) | 67<br>3 | 60<br>22 |
| >N–CH(CH$_3$)–CH(CH$_3$)–N<  meso | 1<br>0.01<br>0.002 | 78<br>72<br>19 |
| >N–CH(CH$_3$)–CH(CH$_3$)–N<  dl | 13<br>3 | 26<br>3 | ii. Mice having implanted tumors Sarcoma 180 and Adenocarcinoma 755, and rats having the implanted tumor Walker 256, are treated with 1,2-bis(3,5-dioxopiperazin-1-yl) ethane. The compound is administered by intraperitoneal injection of a suspension of the substance in isotonic saline containing ½% (w/v) carboxymethyl cellulose. The mice are dosed with 30 mg. of active substance per kilo daily for 5 out of 8 days, and their tumors are exercised and weighed. The rats are given one dose only of 400 mg. per kilo and maintained without further treatment for 8 days when their tumors are also removed and weighed. Compared with control animals typical Treated/Control values of mean tumor weight for the S180 and Ca 755 tumors are in the range of 5–10%, and for the Walker tumors of the order of 20%.

Mice implanted with leukemia L1210 are treated as described above with 30 mg. of active substance per kilo for a continuing period until all the animals succumb. Compared with controls, an increase in survival time of the treatment animals greater than 100% for example of 167%, is obtained.

iii. In tests with tumor S180 similar to those described under (ii) typical Treated/Control values of mean tumor weight for dl-1,2-bis(3,5-dioxopiperazin-1-yl) butane and meso-2,3-bis(3,5-dioxopiperazin-1-yl) butane are 84% at 30 mg./Kg. and 22% at 0.25 mg./Kg. respectively.

In tests with leukemia L1210 similar to those described under (ii) typical Treated/Control values of survival time for these two isomers are 80% at 30 mg./Kg. for the dl isomer and 165% at 0.25 mg./Kg. for the meso isomer.

iv. dl-1,2-bis(3,5-dioxopiperazin-1-yl) propane is fed at 30 mg./Kg. on 5 out of 8 days to mice having S180 tumor and typically gives a Treated/Control value for mean tumor weight of 7%, all the animals surviving and having a weight gain of 12% against 29% in the controls. Against L1210 intraperitoneal and subcutaneous injection at 30 mg./Kg. daily until death typically gives Treated/Control values for survival time of 257% and 223% respectively whilst given orally at 75 mg./Kg. a Treated/Control value of 157% is obtained.

TABLE II

| Isomer of dl-1,2-bis (3,5-dioxopiperazin-1-yl) propane | Non-takes | Survival days | Mean | % Increase of survival time over controls |
|---|---|---|---|---|
| 10% DMSO | 1/10 | 9,9,9,10, 10,10,11, 11,12, | 10.1 | — |
| dl- | 0/10 | 17,17,18, 18,18,18, 19,19,19, 25 | 18.8 | 86 |
| d- | 0/10 | 14,16,16, 17,18,19, 19,25,25, | 19.5 | 93 |

TABLE II-continued

| Isomer of dl-1,2-bis (3,5-dioxopiperazin-1-yl) propane | Non-takes | Survival days | Mean | % Increase of survival time over controls |
|---|---|---|---|---|
| l- | 0/10 | 26 16,17,18, 18,19,20, 21,23,23, 26 | 20.1 | 99 | v. A suspension of leukaemic cells from DBA2 mice heavily infected with leukemia L1210 is obtained by removing ascites from the peritoneal cavity. The ascitic fluid is diluted in saline and injected intraperitoneally at a level of $10^6$ cell into groups of BDFi females.

Stock solutions of each of the dl, d and l isomers of 1,2-bis(3,5-dioxopiperaxin-1-yl)propane in dimethylsulphoxide (DMSO) are prepared and kept frozen. The solutions are thawed each morning and an aliquot diluted 10-fold with saline. Daily intraperitoneal injections of the three diluted solutions into groups of 10 mice are started on the day after innoculation of the leukaemic cells at a daily dosage level of 40 mg./Kg. (equivalent to 0.5 to 1.0 ml of solution per injection). A control group of mice is injected daily with a similar volume of 10% DMSO in saline.

In general, the deaths of mice in any group occur within a few days of each other. If one or more members of a group survive 5 days longer than any other of their companions, injections are stopped and if these mice survive a further 5 days they are classed as failures of transplantation. This is merely an objective criterion of a situation which is visually obvious; the "non-Takes" typically looking sleek and healthy and having no tumor at the inoculation site nor having their bellies swollen with ascitic fluid. Results typical of these obtained are shown in Table II.

EXAMPLE 12

Results of Trials in Human Patients

Various forms of cancer, including lymphosarcomas, fibrosarcomas, carcinomas, lymphoblastic leukemias and Hodgkin's disease, some of which had previously been treated unsuccessfully with other drugs or radiotherapy, have been treated with dl-1.2-bis(3,5-dioxopiperazin-1-yl) propane, whereupon significant regression and palliation of the cancers were obtained.

I claim:
1. A bis(3,5-dioxopiperazin-1-yl) alkane selected from the group consisting of:
   1,2-bis(3,5-dioxopiperazin-1-yl) propane,
   meso-2,3-bis(3,5-dioxopiperazin-1-yl) butane,
   1,2-bis(3,5-dioxopiperazin-1-yl) cyclobutane,
   and acid addition salts thereof with a physiologically acceptable inorganic or organic acid.
2. The bis(3,5-dioxopiperazin-1-yl) alkane of claim 1 which is dl-1,2-bis(3,5-dioxopiperazin-1-yl) propane or an acid addition salt thereof with a physiologically acceptable inorganic or organic acid.
3. The bis(3,5-dioxopiperazin-1-yl) alkane of claim 1 which consists essentially of d-1,2-bis(3,5-dioxopiperazin-1-yl) propane, or an acid addition salt thereof with a physiologically acceptable inorganic or organic acid.
4. The bis(3,5-dioxopiperazin-1-yl) alkane of claim 1 which consists essentially of l-1,2-bis(3,5-dioxopiperazin-1-yl) propane, or an acid addition salt thereof with a physiologically acceptable inorganic or organic acid.
5. The bis(3,5-dioxopiperazin-1-yl) alkane of claim 1 which is meso-2,3-bis(3,5-dioxopiperazin-1-yl) butane, or an acid addition salt thereof with a physiologically acceptable inorganic or organic acid.
6. A bis(3,5-dioxopiperazin-1-yl) alkane acid addition salt of claim 1 which is the hydrochloric, isethionic, tartaric or methane sulphonic acid salt.
7. A process for the preparation of a bis(3,5-dioxopiperazin-1-yl) alkane of claim 1 which comprises heating a compound selected from N,N,N',N'-tetracarboxamidomethyl-1,2-diamino propane, meso-N,N,N',N'-tetracarboxamidomethyl-2,3-diaminobutane and N,N,N',N'-tetracarboxamidomethyl-1,2-diaminocyclobutane with polyphosphoric acid as reagent.

* * * * *